United States Patent [19]

Takano

[11] Patent Number: 4,485,481
[45] Date of Patent: Nov. 27, 1984

[54] COMPUTED TOMOGRAPHIC METHOD

[75] Inventor: Masao Takano, Minami-ashigara, Japan

[73] Assignee: Fuji Photo Film Co., Ltd., Japan

[21] Appl. No.: 428,064

[22] Filed: Sep. 29, 1982

[51] Int. Cl.³ .............................................. G03B 41/16
[52] U.S. Cl. .................................. 378/19; 250/327.2; 378/4
[58] Field of Search .................... 378/19, 4; 250/327.2

[56] References Cited

U.S. PATENT DOCUMENTS 4,439,866  3/1984  Kato ..................................... 378/19

Primary Examiner—Craig E. Church
Attorney, Agent, or Firm—Gerald J. Ferguson, Jr.; Joseph J. Baker

[57] ABSTRACT

In a computed tomographic method in which a tomographic image of an object is composed from many X-ray projection distribution images obtained by exposing a section of the object to X-rays in many different directions, the X-ray projection distribution images obtained by respective exposures to X-rays are once stored at positions different from one another on a stimulable phosphor sheet, the stimulable phosphor sheet is then scanned with a stimulating ray, and a tomographic image of the object is composed by use of electric signals obtained by photoelectrically reading out light emitted from the stimulable phosphor sheet upon stimulation thereof. The stimulable phosphor sheet and an X-ray source are integrally rotated around the object, while the stimulable phosphor sheet is moved approximately at right angles to the plane formed by the rotation thereof.

7 Claims, 2 Drawing Figures

FIG. I
PRIOR ART
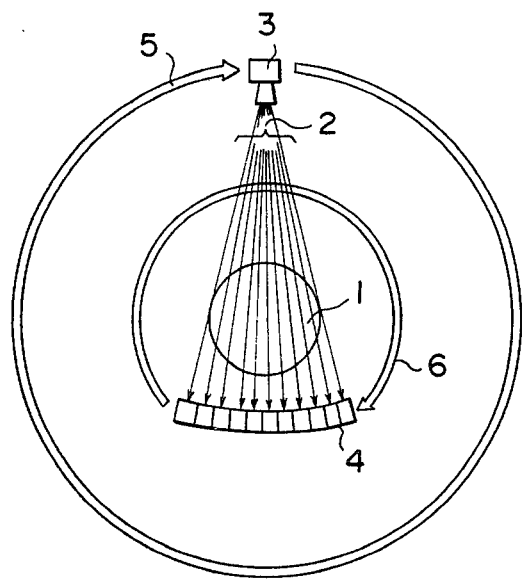
FIG. 2
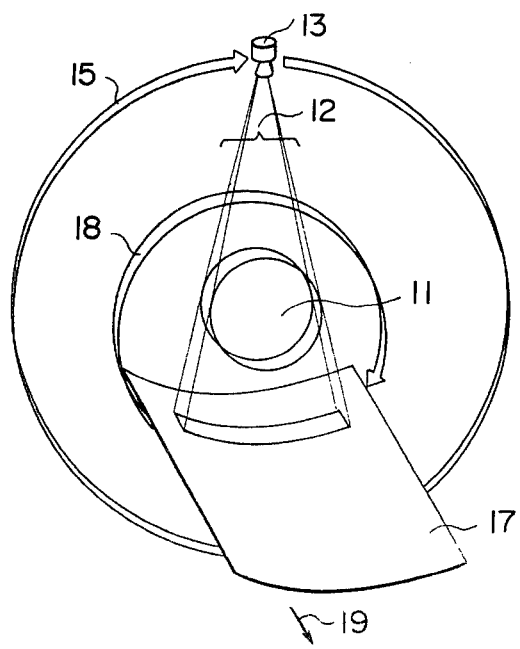

COMPUTED TOMOGRAPHIC METHOD

BACKGROUND OF THE INVENTION

1. Field of the Invention

This invention relates to a computed tomographic method, and more particularly to a computed tomographic method in which a plurality of X-ray projection distribution images obtained by exposing a section of an object to X-rays in many different directions are once stored in a stimulable phosphor sheet, and the stored image information is then scanned with stimulating rays and converted into electric signals to compose a tomographic image of the object.

2. Description of the Prior Art

In a computed tomographic apparatus (hereinafter referred to as a CT apparatus) developed by Hounsfield et al., a tomographic image of a predetermined section of an object is composed from a plurality of X-ray projection distribution images obtained by exposing the section of the object to X-rays in many different directions. The CT apparatus can provide a clear tomographic image of a soft tissue, which could not be obtained with the conventional method using X-ray films, and attracted attention in the field of medical diagnosis.

FIG. 1 shows a typical example of the CT apparatus used at present.

As shown in FIG. 1, the CT apparatus has a tomographic unit comprising an X-ray tube 3 for emitting X-rays 2 of a fan-like distribution (normally spreading at an angle in the range between 30° and 40°) covering a tomographic region 1 where an object is positioned, and a detector 4 for detecting the X-rays 2 transmitting through the object. The detector 4 consists of several hundreds of detecting elements densely positioned to form and arc at an equal distance from the X-ray tube 3. As the detecting elements there are used photomultipliers provided with scintillators on light receiving surfaces, high-pressure xenon gas detecting elements, semiconductor elements, or the like. The X-ray tube 3 and the detector 4 can integrally rotate around the object in the directions of the arrows 5 and 6. The CT apparatus is also provided with a computer for processing the X-ray projection distribution images obtained by detecting the X-rays transmitting through the object by the detector 4.

When taking a tomogram, the X-ray tube 3 and the detector 4 are set at an angle with respect to the object, and X-rays 2 are emitted pulse-wise from the X-ray tube 3. The X-rays 2 transmitting through the object are detected as an X-ray projection distribution image by the detector 4. The X-ray projection distribution image detected is stored in a memory of the computer. After the tomographic operation is finished for one angle with respect to the object, the X-ray tube 3 and the detector 4 are rotated by a small predetermined angle with respect to the object in the directions of the arrows 5 and 6, respectively. The tomographic operation is again conducted as described above to obtain another X-ray projection distribution image, which is then stored in the memory of the computer. The operations mentioned above are repeated to sequentially obtain the X-ray projection distribution images at various predetermined angles with respect to the object. In this way, the operations for obtaining a tomographic image of the object is finished when the X-ray tube 3 and the detector 4 have been rotated one turn (360°) around the object. Then, the information of the X-ray projection distribution images obtained at various angles with respect to the object and stored in the memory of the computer is computed and processed by the computer to obtain a tomographic image of a section of the object.

In another type of CT apparatus, an X-ray tube and a detector consisting of a relatively small number of detecting elements are used to linearly scan an object at an angle with respect to the object. After conducting the linear scanning, the X-ray tube and the detector are rotated by a small predetermined angle with respect to the object, and linear scanning is conducted again. Thereafter, the rotation of the X-ray tube and the detector and the linear scanning are repeated alternately until the tomographic operations are finished when the X-ray tube and the detector have been rotated 180° with respect to the object. There is also a CT apparatus in which detecting elements are positioned in a ring-like from extending 360° around an object, and only the X-ray tube is rotated 360°.

In general, to achieve high diagnostic accuracy and efficiency, the tomographic image should exhibit a spatial resolution sufficient to permit discrimination of details of a tissue. In the conventional CT apparatus described above, the spatial resolution of the tomographic images finally obtained depends on the number of detecting elements of the detector per unit space. However, when photomultipliers provided with scintillators on light receiveing surfaces are used as the detecting elements, a sufficient spatial resolution cannot be obtained because such photomultipliers have a large size and the number thereof per unit space of the detector becomes small. High-pressure xenon gas detecting elements and semiconductor detecting elements can be positioned more densely than the photomultipliers. In this case, however, the available spatial resolution is at most about 1 line/mm. Furthermore, high-pressure xenon gas and semiconductor detecting elements exhibit a lower sensitivity than the photomultipliers provided with scintillators on light receiving surfaces. Therefore, to obtain a tomographic image of the same quality as when using photomultipliers, it is necessary to increase the dose which the object receives. Further, when the detector is formed of a plurality of detecting elements, the respective detecting elements should exhibit the same sensitivity. However, it is technically very difficult to make the detecting elements exhibit exactly the same sensitivity.

Furthermore, in the conventional CT apparatus described above, at least the X-ray tube is intermittently rotated by predetermined angles around the object, and once stopped at the respective angles to apply X-rays to the object and obtain an X-ray projection distribution image. In this case, the time required for the X-ray tube to be moved to change the angle of X-rays with respect to the object constitutes a dead time in the tomographic operation, prolonging the cycle time of tomography. However, an increase in the tomographic time presents a very real problem in cases other than when recording a stationary image of a head, a skeleton, or the like. Namely, when recording an image of an internal organ, the condition of the organ changes due to muscular motion, breathing motion, vermicular motion, or the like during a prolonged tomographic time. As a result, the contrast and the spatial resolution of the tomographic image finally obtained are adversely affected, or noise called artifact occurs, making it impossible to obtain a tomographic image suitable for viewing and diagnostic purposes.

SUMMARY OF THE INVENTION

The primary object of the present invention is to provide a CT method capable of recording a tomographic image with a higher spatial resolution and a higher sensitivity than the conventional CT system.

Another object of the present invention is to provide a CT method capable of being conducted more quickly than the conventional CT system.

The specific object of the present invention is to provide a CT method capable of being conducted by use of a simple apparatus which is small in size and light in weight.

The CT method in accordance with the present invention comprises once storing the X-ray projection distribution images obtained by respective exposures to X-rays at positions on a stimulable phosphor sheet different from one another, scanning said stimulable phosphor sheet with a stimulating ray, and composing a tomographic image of the object by use of electric signals obtained by photoelectrically reading out light emitted from said stimulable phosphor sheet upon stimulation thereof.

In the present invention, the stimulable phosphor sheet is provided with a layer of a stimulable phosphor exhibiting the properties described below. Namely, when the stimulable phosphor is exposed to such radiation as X-rays, $\alpha$-rays, $\beta$-rays, $\gamma$-rays or ultraviolet rays, it stores a part of the energy of the radiation. Then when the phosphor which has been exposed to the radiation is exposed to a stimulating ray such as visible ray, light is emitted from the phosphor in the pattern of the stored energy of the radiation.

The Applicant has proposed a method of reading out radiation image information by use of the stimulable phosphors described above, for example, in his Japanese Unexamined Patent Publication No. 56(1981)-11395 and U.S. Pat. No. 4,258,264. In this method, the stimulable phosphor is first exposed to a radiation to have a radiation image store therein, and is then scanned with a stimulating ray which causes it to emit light in the pattern of the stored image. The light emitted from the stimulable phosphor upon stimulation thereof is photoelectrically detected and converted to an electric signal, which is processed as desired to reproduce a visible image on a recording material such as photographic light-sensitive material or on a display such as cathode ray tube (CRT).

In the radiation image information read-out method described above, the stimulable phosphor develops electrons or positive holes therein in a number proportional to the intensity of X-rays transmitting through the object. The electrons or the positive holes are trapped on the trap level of the stimulable phosphor, thereby storing the X-ray transmission image of the object as the radiation image information in the stimulable phosphor. Thereafter, when the stimulable phosphor is exposed to a stimulating ray, the electrons or the positive holes trapped on the trap level are expelled to emit light upon stimulation. It is known that the intensity of light emitted from the stimulable phosphor upon stimulation thereof is proportional to the number of the electrons or the positive holes trapped therein, i.e. the intensity of X-rays transmitting through the object. Accordingly, the X-ray transmission image can be obtained with a high sensitivity as an electric signal by efficiently collecting light emitted from the stimulable phosphor upon stimulation thereof and photoelectrically converting the collected light by use of a high-sensitivity photodetector shuch as a photomultiplier. It is also known that the stimulable phosphor can exhibit a high spatial resolution, for example 10 lines/mm or more.

In the CT method in accordance with the preset invention, the X-ray projection distribution image is once recorded and stored in the stimulable phosphor sheet. Accordingly, it is not necessary to use a detector consisting of many detecting elements densely positioned, and it is possible to conduct tomography with a high spatial resolution and a high sensitivity. Furthermore, the present invention is free from the problem with regard to fluctuation in sensitivity among detecting elements. It is also possible to continuously rotate the X-ray tube while X-rays are continuously applied therefrom to the object by continuously moving the stimulable phosphor sheet approximately in the direction perpendicular to the plane formed by the rotation of the X-ray tube during tomographic operations. In this way, the present invention can eliminate the dead time, which is inevitably encountered in the conventional CT apparatus, and reduce the tomographic time. Since the tomographic time is short, the condition of the internal organs does not significantly change due to muscular motion, breathing motion, vermicular motion, or the like during the tomographic operations. As a result, the contrast and the spatial resolution of the tomographic image obtained are not adversely affected, and no artifact occurs. Thus, the present invention can provide a tomographic image suitable for viewing and diagnostic purposes. Another advantage of the present invention is that, since the stimulable phosphor sheet extremely light in weight and easy to handle is employed instead of the detector consisting of many X-ray detecting elements, the CT method can be carried out by use of a tomographic apparatus which is simple in construction, small in size and light in weight.

In the present invention, in order to improve the signal-to-noise ratio, it is preferable to use a stimulable phosphor which, when exposed to a stimulating ray, emits light having a wavelength within the range not coinciding with that of the stimulating ray. More specifically, it is preferable that the wavelength of light emitted from the stimulable phosphor upon stimulation thereof be within the range between 300 nm and 500 nm and that of the stimulating ray is within the range between 600nm and 700nm.

As a stimulable phosphor which emits light having a wavelength within the range between 300nm and 500nm and can be employed for the purpose of the present invention, for example, rare earth activated alkaline earth metal fluorohalide phosphor is preferred. One example of this phosphor is, as shown in Japanese Unexamined Patent Publication No. 55(1980)-12143, a phosphor represented by the formula $(Ba_{1-x-y}, Mg_x, Ca_y)FX:aEu^{2+}$ wherein X is at least one of Cl and Br, x and y are numbers satisfying $0 < x+y < 0.6$ and $xy \neq 0$, and a is a number satisfying $10^{-6} \leq a \leq 5 \times 10^{-2}$. Another example of this phosphor is, as shown in Japanese Unexamined Patent Publication No. 55(1980)-12145, a phosphor represented by the formula $(Ba_{1-x}, M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor to be used in this invention can be used ZnS:Cu,Pb; BaQ.xAl$_2$O$_3$:Eu wherein $0.8 \leq x \leq 10$; and M$^{II}$O.xSiO$_2$:A wherein M$^{II}$ is Mg, Ca, Sr, Zn, Cd or Ba, A is Ce, Tb, Eu, Tm, Pb, Tl, Bi or Mn, and x is a number satisfying $0.5 \leq x \leq 2.5$, as shown in Japanese Unexamined Patent Publication No. 55(1980)-12142. Furthermore, as the stimulable phosphor can be used LnOX;xA wherein Ln is at least one of La, Y, Gd and Lu, X is at least one of Cl and Br, A is at least one of Ce and Tb, x is a number satisfying $0 < x < 0.1$, as shown in Japanese Unexamined Patent Publication No. 55(1980)-12144. Among the above numerated phosphors, the rare earth activated alkaline earth metal fluorohalide phosphor is the most preferable, among which barium fluorohalides are the most preferable in view of the high intensity of emission of light.

Further, a barium fluorohalide phosphor added with a metal fluoride as disclosed in Japanese Unexamined Patent Publication Nos. 56(1981)-2385 and 56(1981)-2386, and a barium fluorohalide phosphor containing at least one of a metal chloride, a metal bromide and a metal iodide as desclosed in Japanese Patent Application No. 54(1979)-150873 are also preferable because of the improved light emitting characteristics.

Furthermore, it is also preferable to color the phosphor layer of the stimulable phosphor sheet made of the above phosphor by use of pigments or dyes to improve the sharpness of the image finally obtained, as disclosed in U.S. patent application No. 156,520.

BRIEF DESCRIPTION OF THE DRAWINGS

FIG. 1 is a schematic view showing a conventional CT apparatus, and

FIG. 2 is a schematic view showing an embodiment of the CT apparatus for carrying out the method in accordance with the present invention.

DESCRIPTION OF THE PREFERRED EMBODIMENT

The present invention will hereinbelow be described in further detail with reference to the accompanying drawing.

Referring to FIG. 2 showing an embodiment of the CT apparatus for carrying out the method in accordance with the present invention, an object is positioned in a tomographic region 11, and X-rays 12 are emitted from an X-ray tube 13 in a fan-like form spreading at an angle in the range between about 30° and 40° to include the tomogtaphic region 11. A stimulable phosphor sheet 17 for recording the X-rays 12 transmitting through the object is positioned to form an arc at an equal distance from the X-ray tube 13. The X-ray tube 13 and the stimulable phosphor sheet 17 can integrally rotate around the object in the directions of the arrows 15 and 18, respectively. Further, the stimulable phosphor sheet 17 can be moved in the direction of the arrow 19 approximately at right angles to the plane formed by the rotation of the X-ray tube 13 and the stimulable phosphor sheet 17. In this embodiment, an X-ray tube capable of continuously emitting X-ray is used as the X-ray tube 13.

When taking a tomogram, the X-ray tube 13 and the stimulable phosphor sheet 17 are rotated in the directions of the arrows 15 and 18, respectively, while the X-rays 12 are continuously applied from the X-ray tube 13 to the tomographic region 11. At the same time, the stimulable phosphor sheet 17 is also moved in the direction of the arrow 19. Accordingly, a plurality of X-ray projection distribution images obtained by exposing a predetermined section of the object to the X-rays 12 in a plurality of different directions are sequentially recorded and stored at different positions on the stimulalbe phosphor sheet 17. The tomographi is completed when the X-ray projection distribution image obtained by applying the X-rays 12 in the 360° direction with respect to the object is recorded and stored on the stimulable phosphor sheet 17. Thereafter, the stimulable phosphor sheet 17 carrying the X-ray projection distribution images stored therein is taken out of the tomograph, and scanned with a stimulating ray in a read-out system for reading out the X-ray projection distribution images recorded at various angles with respect to the object. The read-out system may be of the type disclosed in Japanese Unexamined Patent Publication No. 56(1981)-11395. In the read-out system, the stimulable phosphor sheet 17 is scanned in two directions with a stimulating ray such as laser beam, and light emitted from the stimulable phosphor sheet 17 upon stimulation thereof is detected and photoelectrically converted into an electric signal by a photodetector such as photomultiplier. The electric signal thus obtained is then computed and processsed by a computer to compose a tomographic image of the object.

In the embodiment described above, the X-rays 12 are continuously applied from the X-ray tube 13, and the X-ray tube 13 and the stimulable phosphor sheet 17 are continuously moved to eliminate the dead time and reduce the tomographic time. However, it is also possible to intermittently take tomograms at various angles with respect to the object as described above with reference to FIG. 1 showing the conventional CT apparatus.

I claim:

1. A computed tomographic method in which a tomographic image of an object is composed from a plurality of X-ray projection distribution images obtained by exposing a section of the object to X-rays in a plurality of different directions, wherein the improvement comprises once storing the X-ray projection distribution images obtained by respective exposures to X-rays at positions different from one another on a stimulable phosphor sheet, scanning said stimulable phosphor sheet with a stimulating ray, and thereafter composing a tomographic image of the object by use of electric signals obtained by photoelectrically reading out light emitted from said stimulable phosphor sheet upon stimulation thereof.

2. A method as defined in claim 1 wherein said stimulable phosphor sheet is provided with a layer of a stimulable phosphor emitting light having a wavelength within the range between 300nm and 500nm upon stimulation thereof.

3. A method as defined in claim 1 wherein said stimulating ray has a wavelength within the range between 600nm and 700nm.

4. A method as defined in claim 1 wherein said X-rays are applied from an X-ray source in a fan-like form spreading at an angle in the range between about 30° and 40°.

5. A method as defined in claim 1 wherein said stimulable phosphor sheet is positioned to form an arc at an equal distance from an X-ray source.

6. A method as defined in claim 1 wherein said stimulable phosphor sheet and an X-ray source are integrally rotated around the object.

7. A method as defined in claim 6 wherein said stimulable phosphor sheet is also moved approximately at right angles to the plane formed by the rotation of said stimulable phosphor sheet and said X-ray source.

* * * * *